United States Patent [19]

Harnden et al.

[11] 4,049,816
[45] Sept. 20, 1977

[54] ANTIVIRAL 2-AMINO-5-[1-(INDOL-3-YL)ALKYL]-2-THIAZOLIN-4-ONES

[75] Inventors: Michael Raymond Harnden, Horsham; Nicholas David Wright, Westcott, near Dorking, both of England

[73] Assignee: Beecham Group Limited, England

[21] Appl. No.: 666,662

[22] Filed: Mar. 15, 1976

[30] Foreign Application Priority Data

Mar. 24, 1975 United Kingdom ............... 12147/75

[51] Int. Cl.$^2$ .......................................... C07D 275/02
[52] U.S. Cl. .............................. 424/270; 260/306.7 T; 260/326.12 R
[58] Field of Search ................. 260/306.7 T; 424/270

[56] References Cited

U.S. PATENT DOCUMENTS 3,755,316  8/1973  Narayanan et al. .......... 260/306.7 T

*Primary Examiner*—Richard J. Gallagher
*Attorney, Agent, or Firm*—Jacobs & Jacobs

[57] ABSTRACT

Thiazolinone analogues of indolmycin having anti-viral activity as well as a degree of antibacterial and antimycoplasmal activity in contrast to the known indolmycin which has only some antibacterial activity. Tautomers and a single enantiomer or mixture of enantiomers are included. Intermediates are described which are cyclized to produce the active antiviral substances. Suitable dosage forms and amounts are set forth and various routes of administration included including administration to the respiratory tract as by insufflation or inhalation.

24 Claims, No Drawings

ANTIVIRAL 2-AMINO-5-[1-(INDOL-3-YL)ALKYL]-2-THIAZOLIN-4-ONES

This invention relates to novel thiazolinones, to a process for their preparation and to pharmaceutical compositions containing them.

Indolmycin has the formula (I):

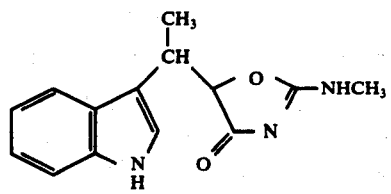

(I)

and has been described in U.K. Pat. No. 862,685 and by Preobrazhenskaya et al. [Tetrahedron, 24 6131, 1968] and Wittenau et al. [J. Amer. Chem. Soc. 83, 4678, 1961 and J. Amer. Chem. Soc. 85, 3425, 1963]. Indolmycin has antibacterial activity but does not have any medically useful anti-viral activity. We have now discovered a series of thiazolinone analogues of indolmycin which possess anti-viral activity as well as a degree of antibacterial and antimycoplasmal activity.

Accordingly the present invention provides a compound of the formula (II):

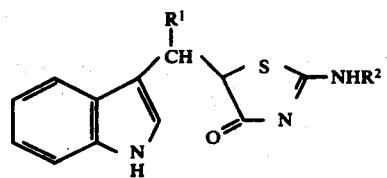

(II)

or a tautomer thereof wherein $R^1$ is a hydrogen atom or a methyl group and $R^2$ is a hydrogen atom or a $C_{1-4}$ alkyl group or a benzyl group optionally substituted by one or two halogen atoms or methoxy or nitro groups.

The tautomers of the compounds of the formula (II) are of the formula (III):

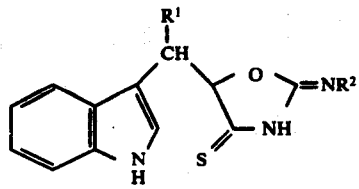

(III)

wherein $R^1$ and $R^2$ are as defined in relation to formula (II).

Normally the compounds of the formula (II) are present with a proportion of the compounds of the formula (III).

The compounds of the formula (II) for the purpose of this invention will have the stereochemistry shown in formula (IV):

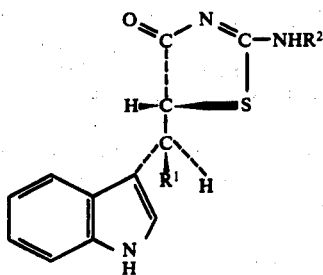

(IV)

or the stereochemistry of the mirror image thereof.

The compounds of this invention may be present either as one enantiomer or as a mixture of the two enantiomers.

Preferably $R^1$ is a methyl group as it is believed that this substitution leads to compounds of particularly acceptable activity.

Most suitably $R^2$ is a hydrogen atom or a methyl, ethyl, propyl or butyl group.

Preferably $R^2$ is a methyl or ethyl group.

The compounds of formula (II) may be prepared by the cyclization of a compound of the formula (V):

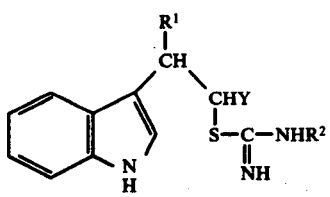

(V)

wherein $R^1$ and $R^2$ are as defined with respect to formula (II) and Y is a group $CO.OY^1$ or $CO.SY^1$ wherein $Y^1$ is a chemically inert group, for example alkyl, aryl, aralkyl.

The reaction is normally carried out in an organic solvent such as a lower alkanol at a non-extreme temperature.

Suitably $Y^1$ is a $C_{1-4}$ alkyl group, for example a methyl group.

Suitably the reaction is carried out at a temperature between 0° and 170°, for example a slightly elevated temperature such as 10°-80° C, for example at room temperature.

Compounds of the formula (V) may be prepared by the reaction of compounds of the formula (VI):

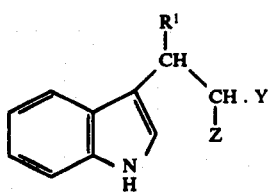

(VI)

wherein $R^1$ and Y are as defined with respect to formula (V) and Z is a group displaceable with a compound of the formula (VII):

  $H_2N.CS.NHR^2$ (VII)

wherein $R^2$ is as defined with respect to formula (II).

The reaction is normally carried out in a suitable solvent at a non-extreme temperature.

Suitably Z is a methanesulphonyloxy group or a chlorine or bromine atom or a chemically equivalent group.

Preferably Z is a chlorine atom when R¹ is a methyl group.

Suitably the reaction is carried out at a low, ambient or slightly elevated temperature, for example, 0°–40° C.

Suitably the solvent is a lower alkanol such as ethanol.

A preferred route to compounds of formula (II) is the reaction of a compound of formula (VI) with a compound of formula (VII) as hereinbefore described to form an intermediate of formula (V) which then cyclizes in situ to form a compound of formula (II).

Suitably the reaction is carried out between 0° and 170°.

Preferably the reaction is carried out between 0° and 80°, for example at room temperature for several days.

Compounds of the formula (II) wherein R¹ and R² are as defined with respect to formula (II) may also be prepared by the isomerization of compounds of the formula (VIII):

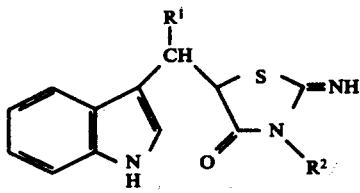

(VII)

wherein R¹ and R² are as defined with respect to formula (II).

This reaction is normally carried out in a suitable solvent in the presence of a base such as sodium methoxide at a non-extreme temperature.

Suitably the solvent is a lower alcohol such as methanol.

Suitably the reaction is carried out at a temperature between 0° and 100° C and preferably between 50° and 100° C.

Compounds of the formula (VIII) are often produced along with compounds of the formula (II) when compounds of the formula (V) are cyclized.

The compounds of the formulae (V) and (VI) are novel intermediates and as such form part of this invention. Preferred intermediates of this invention include the compounds of the formula (VI) wherein Z is a chlorine atom, R¹ is a hydrogen atom or a methyl group and Y is a CO₂R³ group wherein R³ is a C₁₋₄ alkyl group.

The compositions of this invention may be administered topically or systemically, for example orally, by injection, infusion, insufflation or aerosol.

A particularly suitable method of administration is direct administration into the respiratory system by means of insufflation or inhalation, for example, of a powder, or aerosol or nose drops. An alternative particularly suitable method of administration is oral administration.

Typical oral formulations will include tablets, capsules, sachets and the like. Where appropriate and where necessary the formulations may include diluents, binding agents, dispersing agents, surface-active agents, lubricating agents, coating materials or other pharmaceutically acceptable additives in conventional manner. Where the formulations are tablets, capsules or sachets and the like they will represent premeasured unit doses but in the case of suspensions and the like the formulations may be presented as pre-measured unit doses or in multi-dose containers from which the appropriate unit dose may be withdrawn.

The injectable form may be, for example, an aqueous or non-aqueous solution in a pharmaceutically acceptable liquid.

Suitable formulations for administration into the respiratory tract will include snuff or like formulations, or aerosols and capsules filled with an insufflatable powder. Such powders may consist essentially of a compound of formula (II) or of mixtures of a compound of formula (II) and an inert carrier material such as lactose or the like. In the latter case it is often useful to have the compound of formula (II) adsorbed onto the surface of the carrier particles. Generally, the compound of formula (II) will be present as particles of small diameters, for example 5 microns or less. The capsules may be of any suitable material such as hard gelatin or the like which may be readily broached to allow egress of their contents.

Suitably the compounds of formula (II) may be administered at a rate of from 2.5 to 100mg/kg/day. Generally, the daily dose is administered in from 2 to 5 installments.

More suitably the daily dose is from 10 to 80 mg/kg and preferably the daily dose is from 20 to 50 mg/kg.

Unit dosage forms normally contain from 50 to 1000 mgs, more usually from 100 to 500 mgs and generally from 50 to 300 mgs.

The dl-compound of the formula (II) wherein R¹ and R² are both methyl groups did not show overt toxic effects in mice when administered as a single dose of 640mg/kg intraperitoneally nor when dosed twice a day on each of three consecutive days with 100mg/kg subcutaneously or orally.

The dl-compound of the formula (II) wherein R¹ and R² are both methyl groups was found to have an MIC of about 2μg/ml when tested against strains. *Staphylococcus aureus* and *Streptococcus faecalis* and about 4μg/ml when tested against a strain of *Mycoplasmia pneumoniae*.

Compounds of the formula (II) were evaluated against Coxsackie BI virus and Rhinovirus type 2 in monolayers of Hela Ohio cells and against Influenza Ao NWS strain in monolayers of Baby Hampster Kidney (BHK 21) Cells. The inhibition of virus plaque formation in these systems was determined and the results are shown in Tables 1 and 2.

$$\% \text{ plaque reduction} = \frac{\text{No. of plaques in virus control} - \text{No. of plaques in treated}}{\text{No. of plaques in virus control}} \times 100$$

The dl-compound of the formula (II) wherein R¹ and R² are both methyl groups was evaluated against the Hong Kong strain of Influenza A2 virus (A/HK/1/68; H3N2) in male albino CD1 mice. The mice were infected by exposure to a virus aerosol and the compound administered subcutaneously and orally to different groups for 3 days. Eight days after infection the mice were killed and their body weight and lung weight determined. The results are shown in Table 3.

The following examples illustrate the preparation of the compounds of the present invention:

EXAMPLE 1 d-α-Indolmycinic Acid and 1-α-Indolmycinic Acid a. Resolution dl-α-Indolmycinic acid (33.8 g) was dissolved in acetone (300 ml)/methylene chloride (300 ml) and a solution of 1-α-phenylethylamine (18.7 g, $[\alpha]_D^{20} = -39°$) in methylene chloride (75 ml) added.

The solution was concentrated at reduced pressure and ethyl acetate (250 ml) added. On storage at 5° C overnight, white crystals were obtained. These were filtered, dried in vacuo (47.7 g, 91% yield), and recrystallized twice from acetone, yielding the 1-α-indolmycinic acid 1-α-phenylethylamine salt (16.92 g) as white crystals, m.p. 173°-175°, $[\alpha]_D^{20} = -21.5°$ (c10 in methanol).

The acetone solutions were combined and concentrated in vacuo to a gum. The gum was dissolved in ethyl acetate (1 lit), washed with $N/_{10}$ hydrochloric acid (100 ml) and water (100 ml), dried (MgSO$_4$) and concentrated in vacuo. The solid thus obtained was recrystallized from dichloroethane (1.2 lit), yielding crude d-α-indolmycinic acid (14.06 g) as an off-white solid. This solid was dissolved in acetone (100 ml)/methylene chloride (100 ml) and a solution of d-α-phenylethylamine (7.78 g, $[\alpha]_D^{20} = +39°$) in methylene chloride (20 ml) added.

The solution was concentrated at reduced pressure and ethyl acetate (100 ml) added. On storage at 5° C overnight white crystals were obtained. These were filtered, dried in vacuo and recrystallised twice from acetone, yielding the d-α-indolmycinic acid d-α-phenylethylamine salt (13.74 g, m.p. 174°-6°, $[\alpha]_D^{20} = +21.6°$ (c10 in methanol).

b. Liberation of Optically Active Acids

The α-indolmycinic acid α-phenylethylamine salt (16.8 g) was suspended in ethyl acetate (200 ml) and shaken with $N/_2$ hydrochloric acid (100 ml). The ethyl acetate solution was dried (MgSO$_4$) and concentrated in vacuo to a white solid, which was triturated with 1,2-dichloroethane (50 ml), filtered and dried, yielding l-α-indolmycinic acid (93% recovery), m.p. 176°-7°, $[\alpha]_D^{20} = -9.3°$ (c10 in methanol) or d-α-indolmycinic acid (90% recovery), m.p. 176°-7°, $[\alpha]_D^{20} = +9.3°$ (c10 in methanol). The infrared and nmr spectra of the 2 optically active α-indolmycinic acids were identical to those of dl-α-indolmycinic acid.

EXAMPLE 2 d- and l- Methyl α-Indolmycinate

A solution of the α-indolymycinic acid enantiomer (4.6 g) and p-toluene sulphonic acid (4.1 g) in methanol (100 ml) was boiled under reflux for 18 hours. The solution was cooled and concentrated in vacuo. The residue was dissolved in ethyl acetate (100 ml) and the solution washed with 5% sodium carbonate (40 ml) and water (2 × 40 ml), dried (MgSO$_4$) and concentrated in vacuo. A clear oil was obtained which was dissolved in benzene (30 ml) and upon storage at 5° C for 3 hours yielded white crystals of the methyl ester enantiomer.

l -Methyl α-indolmycinate (4.6 g, 94% yield), m.p. 80°-81° C $[\alpha]_D^{20} = -3.6°$ (c10 in methanol).

d -Methyl α-indolmycinate (4.5 g, 92% yield), m.p. 80°-81° C $[\alpha]_D^{20} = +3.6°$ (c10 in methanol).

The infrared and $^1$H nmr spectra of both enantiomers were identical to those of dl-methyl α-indolmycinate, indicating that no epimerisation had occurred during esterification.

EXAMPLE 3 dl-Methyl α-2-chloro-3-(3-indolyl) butyrate

To a solution of dl-methyl α-indolmycinate (4.7 g) in dry pyridine (50 ml) at 0° C, was added methanesulphonyl chloride (3.1 ml). The mixture was stored at 5° C for 3 days and then poured into iced water (230 ml). The mixture was extracted with ether (4 × 200 ml) and the combined ether solutions washed with 5N hydrochloric acid (3 × 200 ml) and water (2 × 200 ml), and dried over anhydrous Na$_2$SO$_4$. Removal of the ether in vacuo gave a yellow oil (4.8 g) which crystallized on scratching. Recrystallization from ether followed by filtration, washing with ether:cyclohexane (1:1) and drying in vacuo, gave white plates of dl-methyl α-2-chloro-3-(3-indolyl) butyrate (3.1 g, 60% yield), m.p. 98°-100° C. I.R.νmax. 3320 (NH), 1732 (C═O) cm$^{-1}$ (Nujol).

EXAMPLE 4 d-Methyl α-2-chloro-3-(3-indolyl) butyrate and l-methyl α-2-chloro-3-(3-indolyl) butyrate To a solution of the methyl α-indolmycinate enantiomer (2.3 g) in dry pyridine (20 ml) at 0° C, was added a solution of benzylmethylammonium chloride (0.24 g) in chloroform (2 ml), followed by dropwise addition of methanesulphonyl chloride (1.6 ml). The mixture was stored at 0°-5° C for 3½ days and then poured into iced water (150 ml). After extraction into chloroform (3 × 50 ml), the combined organic solutions were stirred vigorously with 5N HCl (ca. 50ml) for 15 minutes, washed with water (2 × 50 ml) and then dried (MgSO$_4$). Removal of solvent in vacuo gave a yellow oil which was extracted into dry ether (2 × 100 ml). After filtering, the solution was concentrated to ca. 30 ml., and cooled to 0°-5° C for 3 hours yielding white plates of the 2-chloroester enantiomer.

These were recrystallized from ether and yielded:

l -Methyl α-2-chloro-3-(3-indolyl) butyrate (1.27 g, 51% yield), m.p. 123°-125°, $[\alpha]_D^{20} = -2.6°$ (c10 in dioxane)

d-Methyl α-2-chloro-3-(3-indolyl) butyrate (1.69 g, 68% yield), m.p. 124°-126°, $[\alpha]_D^{20} = +2.6°$ (c10 in dioxane).

The infrared and $^1$H nmr spectra of both enantiomers were identical to those of dl-methyl α-2-chloro-3-(3-indolyl)buryrate, indicating that no epimerization had occured under the reaction conditions used.

EXAMPLE 5 dl-Methyl 2-mesyloxy-3-(3-indolyl) propionate

To a solution of dl-methyl 3-(3-indolyl) lactate (11 g) in dry pyridine (250 ml) at 0° C, methanesulphonyl chloride (8 ml) was added. The mixture was stored at 5° C for 3 days and then poured into iced water (1 liter). The mixture was extracted with ether (4 × 500 ml) and the combined ether solutions washed with 5N hydrochloric acid (500 ml) and water (2 × 500 ml), dried over anhydrous Na$_2$SO$_4$ and concentrated in vacuo to an oil (12.8 g). Upon trituration with benzene (150 ml) the oil yielded white crystals. The mixture was stored at 5° C for 2 hours, the crystals collected and dried in vacuo, yielding 9.9 g (67% yield) of dl-methyl 2-mesyloxy-3-

(3-indolyl) propionate, m.p. 89°–90° C. I.R.ν max. 3430 (NH), 1760 (ester C=O), 1368 (SO$_2$), 1165 (SO$_2$) cm$^{-1}$ (Nujol)

EXAMPLE 6 dl-2-Amino-5-[(3-indolyl)methyl]-2-thiazolin-4-one

A solution of dl-methyl 2-mesyloxy-3-(3-indolyl) propionate (2.97 g) and thiourea (0.76 g) in ethanol (100 ml) was refluxed for 6 hours. The ethanol was removed in vacuo and a solution of sodium acetate (1.64 g) in water (200 ml) added. The white solid which precipitated was collected and after dissolution in ethanol, was cooled to 0° C. The white crystals were filtered off and dried in vacuo, yielding 1.73 g (71% yield) of dl-2-amino-5-[(3-indolyl)methyl]-2-thiazoline-4-one, m.p. 220°–223° C (decomp.) I.R.ν max. 3430, 3150(NH), 1675 (C=O), 1630 (C=N) cm$^{-1}$ (Nujol)

EXAMPLE 7 dl-2-Methylamino-5-[(3-indolyl)methyl]-2-thiazolin-4-one

A solution of dl-methyl 2-mesyloxy-3-(3-indolyl)propionate (1.49 g) and N-methylthiourea (0.45 g) in ethanol (60 ml) was refluxed for 3 hours. A solution of sodium (0.23 g) in ethanol (20 ml) was then added and the combined solution refluxed for a further 3 hours. After cooling, the solution was added to water (240 ml) containing glacial acetic acid (0.6 g). The precipitate formed was filtered off, and dried in vacuo (1.12 g). This was then dissolved in ethyl acetate (2 ml) and chromatographed on silica gel (Kieselgel H, type 60, 70 ml) using ethyl acetate to elute a yellow band followed by methanol to elute a second yellow band. Removal of solvent from this second band gave an oil which was dissolved in ethyl acetate (5 ml) and cooled to 0° C. The pale yellow crystals were filtered off, washed with ethyl acetate and then petroleum spirit (b.p. 40°–60° C) to give dl-2-methylamino-5-[(3-indolyl)methyl]-2-thiazolin-4-one (0.315 g, 24% yield), m.p. 181°–183° C. I.R. ν max. 3350 (NH), 1680 (C=O), 1620 (C=N) cm$^{-1}$ (Nujol)

EXAMPLE 8 dl-2-Imino-5-[(3-indolyl)methyl]-3-methyl-thiazolidin-4-one

A solution of dl-methyl 2-mesyloxy-3-(3-indolyl propionate (1.49 g) and N-methylthiourea (0.45 g) in methanol (50 ml) was maintained at 20° C for 2 weeks. The methanol was removed in vacuo and water (100 ml) added to the residue. A small quantity of white precipitate was filtered from the aqueous solution (pH 3), which was then brought to pH 7 by addition of M sodium carbonate. A white precipitate was obtained which was filtered and dried in vacuo (0.64 g). Thin layer chromatography (silica, eluted with ethyl acetate) indicated that this material contained a major component at R$_f$0.45 and a minor one at R$_f$0.10. [In the same system, dl-2-methylamino-5-[(3-indolyl)methyl]-2-thiazolin-4-one (example 12) has R$_f$0.10.]

The solid was chromatographed on silica (Kieselgel H, type 60) eluted with ethyl acetate. Upon concentration of the fractions containing the faster moving component and cooling to 0°, 0.5 g (38.5% yield) of pure dl-2-imino-5-[(3-indolyl)methyl]-3-methyl-thiazolidin-4-one, m.p. 142°–4° C, was obtained. I.R. ν max. 3375, 3250 (NH), 1698 (C=O), 1615 (C=N) cm$^{-1}$ (Nujol).

EXAMPLE 9

Rearrangement of dl-2-Imino-5-[(3-indolyl)methyl]-3-methylthiazolidin-4-one to dl-2-Methylamino-5-[(3-indolyl)methyl]-2-thiazolin-4-one A solution of dl-2-imino-5-[(3-indolyl)methyl]-3-methyl-thiazolidin-4-one (0.10 g) in methanol (5 ml) was treated with a catalytic amount of sodium hydride (2 mg). The solution was gently refluxed for 2 hours under nitrogen. After cooling, water (10 ml) was added, and the solution was neutralised with dilute hydrochloric acid. Evaportion of solvents in vacuo gave a yellow oil, which after dissolution in ethyl acetate, was chromatographed on silica gel (Kieselgel H, type 60) using ethyl acetate to elute a yellow band (containing a trace of starting material), followed by methanol to elute a second yellow band. Evaporation of solvent from this second band gave a yellow oil (0.1 g) which was dissolved in warm ethyl acetate and then cooled to 0° C. The white crystals were filtered off, washed with ethyl acetate and petroleum spirit (b.p. 40°–60° C) and dried in vacuo, yielding 72 mg (72%) of dl-2-methylamino-5-[(3-indolyl)methyl]-2-thiazolin-4-one, m.p. 181°–183° C. (Identical with product from Example 7)

EXAMPLE 10 dl-2-Ethylamino-5-[(3-indolyl)methyl]-2-thiazolin-4-one

A solution of dl-methyl 2-mesyloxy-3-(3-indolyl) propionate (1.49 g) and N-ethylthiourea (0.52 g) in ethanol (50 ml) was maintained at room temperature for 8 days. The solvent was removed in vacuo to give a yellow oil to which water (50 ml) was added. The solution was then basified by addition of M sodium carbonate. The white precipitate formed was filtered off, redissolved in chloroform and dried (MgSO$_4$). Removal of the chloroform in vacuo gave a pale yellow oil which was dissolved in ethyl acetate (ca. 8 ml) and colled to 0°. The white crystals were filtered off, washed with ether and dried in vacuo to give dl-2-ethylamino-5-[(3-indolyl)methyl]-2-thiazolin-4-one (0.53 g, 41%) R$_f$ (silica/ethyl acetate) 0.13, m.p. 173°–175° C. I.R. ν max. 3380 (NH), 1692 (C=O), 1610 (C=N)cm$^{-1}$ (Nujol)

EXAMPLE 11 dl-α-2-Amino-5-[1-(3-indolyl)ethyl]-2-thiazolin-4-one

A solution of dl-methyl α-2-chloro-3-(3-indolyl) butyrate (0.5 g) and thiourea (0.15 g) in ethanol (50 ml) was maintained at 20° C for 2.5 days. The solvent was then moved in vacuo to give an orange oil to which water (50 ml) was added. M sodium carbonate (8 ml) was then added so that a basic solution was formed. The white precipitate was then filtered off, dissolved in ethyl acetate (100 ml) and dried (MgSO$_4$). After filtration, and removal of solvent in vacuo, an oily solid (2.4 g) was formed. This was dissolved in methanol (8 ml) filtered and cooled to 0°. The white crystals were filtered off and washed with ethyl acetate and petroleum spirit (b.p. 40°–60° C) to give dl-α-2-amino-5-[1-(3-indolyl) ethyl]-2-thiazolin-4-one, 0.28 g (53% yield), m.p. 228°–230° C.

EXAMPLE 12 dl-α-2-Methylamino-5-[1-(3-indolyl)ethyl]-2-thiazolin-4-one

A solution of dl-methyl α-2-chloro-3-(3-indolyl) butyrate (0.5 g) and N-methylthiourea (0.18 g) in ethanol (50 ml) was maintained at room temperature for 8 days. The solvent was removed in vacuo to give a yellow oil to which water (50 ml) was added. The solution was then basified by addition of M sodium carbonate, and the white precipitate formed (0.5 g) was filtered off, washed with water and dried in vacuo. [This solid showed two components on t.l.c. (silica/ethyl acetate) with $R_f$ values 0.42 and 0.10.]

The precipitate was dissolved in methanol (30 ml) and, after addition of N sodium hydroxide (0.1 ml), the solution was refluxed for 8 hours. After cooling, water (20 ml) was added, and the solution brought to pH 8 by addition of dilute hydrochloric acid. Removal of solvent in vacuo gave a yellow oil which was dissolved in the minimum of warm methanol: ethyl acetate (1:1) and chromatographed on silica (Kieselgel H, type 60, 70 ml) using ethyl acetate to elute a yellow band, and then methanol to elute a second yellow band. This second band was concentrated to an oil, dissolved in hot ethyl acetate and cooled to 0° C. The white crystals were filtered off, washed with ethyl acetate and petroleum spirit (b.p. 40°–60°) and dried in vacuo, yielding dl-α-2-methylamino-5[1-(3-indolyl) ethyl]-2-thiazolin-4-one (0.25 g, 46% yield) $R_f$ (conditions as above) 0.10, m.p. 208°–210°. I.R. ν max. 3200 (br) (NH), 1680 (C=O), 1590 (C=N), cm$^{-1}$ (Nujol).

EXAMPLE 13 dl-α-2-Ethylamino-5-[1-(3-indolyl)ethyl]-2-thiazolin-4-one

A solution of dl-methyl α-2-chloro-3-(3-indolyl)butyrate (0.75 g) and N-ethylthiourea (0.36 g) in ethanol (75 ml) was maintained at room temperature for 6 days. The solvent was then removed in vacuo and then sodium carbonate (3 ml) was added followed by water (50 ml). The initially formed oil became sufficiently solid after 10 minutes to be filtered from the solution. It was then washed with water, dissolved in warm ethyl acetate (50 ml) and dried (MgSO$_4$).

After filtering, removal of solvent in vacuo gave a yellow oil (0.8 g) which showed four components on thin-layer chromatography (silica/ethyl acetate) with $R_f$ values 0.59, 0.53, 0.31 and 0.17. Chromatography on silica gel (Kieselgel H, type 60, 80 ml) using ethyl acetate to elute a pale yellow band, gave dl-α-2-ethylamino-5-[1-(3-indolyl)ethyl]-2-thiazolin-4-one as a white crystalline solid, (0.12 g, 14%), m.p. 195°–7°, ($R_f$ (as above) 0.17) from ethyl acetate. I.R. ν max. 3260 br. (NH), 1678 (C=O), 1585 (C=N) cm$^{-1}$ (Nujol).

EXAMPLE 14 d- and 1-2-Methylamino-5-[1-(3-indolyl) ethyl]-2-thiazolin-4-one

To a solution of the methyl α-2-chloro-3-(3-indolyl) butyrate enantiomer (0.68 g) in methanol (30 ml) was added a solution of N-methylthiourea (0.25 g) in methanol (20 ml) and the mixture was maintained at 20° for 3 days. The solvent was then removed in vacuo to give a yellow oil to which water (50 ml) and M sodium carbonate (3 ml) were added. The white precipitate formed was filtered off, washed with water and dried in vacuo.

This precipitate was dissolved in methanol (50 ml) and, after addition of N sodium hydroxide (0.1 ml), the solution was refluxed for 3 hours. After cooling, water was added (20 ml) and the solution brought to pH 8 by addition of N hydrochloric acid. Removal of solvent in vacuo gave a yellow oil which was dissolved in the minimum of warm methanol, and, after filtering, was cooled to 0° – 5° C.

In the case of the product from the laevorotatory chloroester enantiomer, white crystals were obtained at this stage, and these were filtered off, and recrystallised from methanol to give 1-2-methylamino-5-[1-(3-indolyl)ethyl]-2-thiazolin-4-one (0.22 g, 30% yield), m.p. 225°–227°, $[\alpha]_D^{20} = -100.7°$ (c. 0.3 in methanol).

After chromatography of the filtrate on silica (Kieselgel H, type 60, 70 ml) using ethyl acetate to elute one component, followed by methanol to elute a second component, the solutions containing this second component were concentrated to an oil. This was dissolved in hot ethyl acetate and the solution cooled to 0° C to give a further crop (0.14 g, 19% yield of the l-enantiomer, identical with the above.

In the case of the product from the dextrorotatory chloroester enantiomer, no crystallization occurred prior to chromatography. However, using the same conditions for chromatography as above, but with 100 ml of Kieselgel H, the methanol eluted component gave a yellow oil, which, after two crystallizations from methanol, gave white crystals of d-2-methylamino-5-[1-(3-indolyl) ethyl]-2-thiazolin-4-one (0.18 g, 25% yield), m.p. 226° – 228°, $[\alpha]_D^{20} = +101.4°$ (c. 0.3 in methanol).

The infra-red and $^1$H n.m.r. spectra of both enantiomers were identical o those of dl-2-methylamino-5-[1-(3-indolyl) ethyl]-2-thiazolin-4-one, indicating that no epimerization had occurred under the reaction conditions used.

Table 1

| | | % plaque reduction at conc given (μg/ml) | | |
|---|---|---|---|---|
| Virus | Compound | 30 | 10 | 3 |
| Coxsackie B1 66TCF strain | compound of formula (II) wherein $R_1$, $R_2$ = Me | 100 | 100 | 0 |
| | hydroxybenzylbenzimidazole | 100 | 0 | 0 |
| Coxsackie B1 (GP strain) Pool 40 mouse adapted strain | compound of formula (II) wherein $R_1$, $R_2$ = Me | 100 | 100 | 0 |
| | hydroxybenzylbenzimidazole | 91 | 17 | 0 |
| Rhinovirus type 2 | compound of formula (II) wherein $R_1$, $R_2$ = Me | * | 85 | 0 |
| | hydroxybenzylbenzimidazole | 50 | 23 | 0 |

*cell metabolism and viral replication inhibited at this concentration

Table 2

| Compound of formula (II) | | % plaque reduction at conc. given (μg/ml) | | | |
|---|---|---|---|---|---|
| $R_1$ | $R_2$ | 30 | 10 | 3 | 1 |
| H | CH$_3$ | * | 36 | 0 | 0 |
| CH$_3$ | H | 46 | 33 | 0 | 0 |
| CH$_3$ | CH$_3$ | * | * | 80 | 54 |
| CH$_3$ | C$_2$H$_5$ | * | * | 96 | 34 |
| 1-aminoadamantane | | 92 | 72 | 62 | 50 |

*cell metabolism and viral replication inhibited at this concentration

Table 3

| In-vivo inhibition of influenza A2 virus | | | |
| --- | --- | --- | --- |
| Compound | Administration Route | Dosage (mg/kg) 2x days 0, 1, 2 | Activity day 8, lung wt/body wt ratio × 100 |
| Infected controls | — | — | 1.08 |
| Compound of formula (II) wherein $R_1, R_2$ = Me | S.C. | 30 | 0.97 |
| | S.C. | 100 | 0.96 |
| | P.O. | 30 | 1.00 |
| | P.O. | 100 | 0.89 |
| Uninfected controls | — | — | 0.72 |

We claim:

1. A compound of the formula (II):

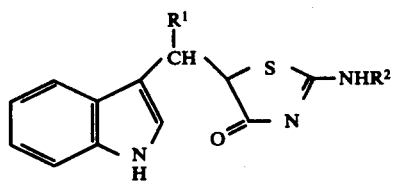

(II)

or a tautomer thereof wherein $R^1$ is hydrogen or methyl and $R^2$ is hydrogen, alkyl of 1 to 4 carbon atoms, or benzyl unsubstituted or substituted by one or two halogen atoms, methoxy or nitro groups.

2. A compound according to claim 1 wherein $R^1$ is methyl and $R^2$ is hydrogen, methyl, ethyl, propyl or butyl.

3. A compound according to claim 2 wherein $R^2$ is methyl or ethyl.

4. The compound according to claim 1 which is dl-2-amino-4-[(3-indolyl)methyl]-2-thiazolin-4-one.

5. The compound according to claim 1 which is dl-2-methylamino-5-[(3-indolyl)methyl]-2-thiazolin-4-one.

6. The compound according to claim 1 which is dl-2-ethylamino-5-[(3-indolyl)methyl]-2-thiazolin-4-one.

7. The compound according to claim 1 which is dl-α-2-amino-5-[1-(3-indolyl)ethyl]-2-thiazolin-4-one.

8. The compound according to claim 1 which is dl-α-2-methylamino-5-[1-(3-indolyl)ethyl]-2-thiazolin-4-one.

9. The compound according to claim 1 which is dl-α-2-ethylamino-5-[1-(3-indolyl)ethyl]-2-thiazolin-4-one.

10. The compound according to claim 1 which is d-2-methylamino-5-[1-(3-indolyl)ethyl]-2-thiazolin-4-one.

11. The compound according to claim 1 which is 1-2-methylamino-5-[1-(3-indolyl)ethyl]-2-thiazolin-4-one.

12. A pharmaceutical composition useful for combatting infections caused by an RNA virus in the respiratory system of humans and animals which comprises an anti-virally effective amount of a compound of the formula (II):

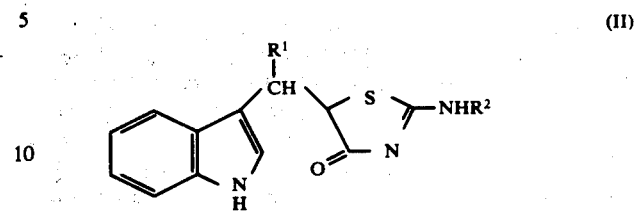

(II)

or a tautomer thereof wherein $R^1$ is hydrogen or methyl and $R^2$ is hydrogen, alkyl of 1 to 4 carbon atoms, or benzyl unsubstituted or substituted by one or two halogen atoms, methoxy or nitro groups, in combination with a pharmaceutically acceptable carrier.

13. A composition according to claim 12 wherein $R^1$ is methyl and $R^2$ is hydrogen, methyl, ethyl, propyl or butyl.

14. A composition according to claim 12 wherein $R^2$ is methyl or ethyl.

15. A composition according to claim 12 wherein the compound is dl-2-amino-4-[(3-indolyl)methyl]-2-thiazolin-4-one.

16. A composition according to claim 12 wherein the compound is dl-2-methylamino-5-[(3-indolyl)methyl]-2-thiazolin-4-one.

17. A composition according to claim 12 wherein the compound is dl-2-ethylamino-5-[(3-indolyl)methyl]-2-thiazolin-4-one.

18. A composition according to claim 12 wherein the compound is dl-α-2-amino-5-[1-(3-indolyl)ethyl]-2-thiazolin-4-one.

19. A composition according to claim 12 wherein the compound is dl-α-2-methylamino-5-[1-(3-indolyl)ethyl]-2-thiazolin-4-one.

20. A composition according to claim 12 wherein the compound is dl-α-2-ethylamino-5-[1-(3-indolyl)ethyl]-2-thiazolin-4-one.

21. A composition according to claim 12 wherein the compound is d-2-methylamino-5-[1-(3-indolyl)ethyl]-2-thiazolin-4-one.

22. A composition according to claim 12 wherein the compound is 1-2-methylamino-5-[1-(3-indolyl)ethyl]-2-thiazolin-4-one.

23. A pharmaceutical composition according to claim 12 in oral administration form.

24. A pharmaceutical composition according to claim 12 in a form suitable for insufflation or inhalation administration into the respiratory system.

* * * * *